US007288083B2

(12) United States Patent
Holman

(10) Patent No.: US 7,288,083 B2

(45) Date of Patent: Oct. 30, 2007

(54) NASAL-NASOPHARYNGEAL IRRIGATING AND CLEANSING SYSTEM

(76) Inventor: Andrew W. Holman, 24230 Archwood St., West Hills, CA (US) 91307

( * ) Notice: Subject to any disclaimer, the term of this patent is extended or adjusted under 35 U.S.C. 154(b) by 539 days.

(21) Appl. No.: 10/726,910

(22) Filed: Dec. 4, 2003

(65) Prior Publication Data

US 2005/0124974 A1 Jun. 9, 2005

(51) Int. Cl.
*A61M 31/00* (2006.01)
*A61M 1/06* (2006.01)

(52) U.S. Cl. ........................................ 604/514; 604/73

(58) Field of Classification Search .................. 604/73, 604/94.01, 181, 131, 514, 257, 48, 19, 212, 604/41, 78; 229/400–405
See application file for complete search history.

(56) References Cited

U.S. PATENT DOCUMENTS

| | | | | |
|---|---|---|---|---|
| 4,216,769 A * | 8/1980 | Grimes | .................. | 128/207.13 |
| 5,112,322 A * | 5/1992 | Hathaway | ................... | 604/317 |
| 5,208,896 A * | 5/1993 | Katayev | ..................... | 392/444 |
| 5,417,652 A * | 5/1995 | Scott, Sr. | ..................... | 604/19 |
| D377,091 S * | 12/1996 | Scott, Sr. | ................... | D24/121 |
| 5,911,504 A * | 6/1999 | Schindlegger, Jr. | ......... | 366/197 |
| 6,412,488 B1 * | 7/2002 | Barnett et al. | ......... | 128/207.13 |
| 6,776,778 B2 * | 8/2004 | Prince | ........................ | 604/514 |
| 2002/0077621 A1 * | 6/2002 | Prince | ........................ | 604/514 |
| 2004/0091556 A1 * | 5/2004 | Tigunait et al. | ............. | 424/725 |

* cited by examiner

*Primary Examiner*—Catherine S. Williams
(74) *Attorney, Agent, or Firm*—Matthew F. Jodziewicz

(57) ABSTRACT

A nasal-nasopharyngeal irrigating and cleansing system including a cup with one or more assemblies that allow the flow and control of various irrigating, cleansing and medicinal liquids into the nasal passages. The construction of the cup provides sealing surfaces to allow the controlled flow of the liquids into the nose through either nostril without spillage. The flow of the liquid through the nasal passages removes via abrasion any virus or irritant substances that may be in the nasal passages or on the nasal membranes. According to one aspect of the invention as the liquid is dispensed, the angle of the cup to the face changes but a sealing rim on the cup wall continues to seal to the user's face as the angle of the cup to the user's face changes, allowing liquid to be drawn up into the user's nose via vacuum or gravity. A method of using the device of the invention for irrigating, cleansing and coating the nasal passages with antiviral agents or other beneficial medicines.

10 Claims, 6 Drawing Sheets

NASAL-NASOPHARYNGEAL IRRIGATING AND CLEANSING SYSTEM

BACKGROUND OF THE INVENTION

1. Field of the Invention

This invention relates generally to nasal-nasopharyngeal-irrigation and -cleaning (NNIC) systems that are used to remove harmful substances from human nasal and nasopharyngeal cavities, and, more particularly, to a device for holding fluid and administering fluid to the nasal-nasopharyngeal cavities. The fluid may be for washing or irrigating the nasal-nasopharyngeal cavities or may be a medicinal preparation for treating a condition by ingestion through the nose and its nasal-nasopharyngeal cavities. The invention also relates to a method for irrigating and washing the nasal-nasopharyngeal cavities and for ingesting a medicinal prepation through the nose and its nasal-nasopharyngeal cavities.

2. Description of the Prior Art

It is desirable for the treatment of certain conditions, especially conditions affecting the nasal-nasopharyngeal cavities and certain diseases which are manifested or contacted in or through the nasal-nasopharyngeal cavities, to wash, irrigate, and/or apply a fluid medicinal preparation to the nasal-nasopharyngeal cavities and passages.

Previously these washing, irrigating and applying operations have been accomplished using a spray bottle or similar device which is manually squeezed to force the contents of the bottle out of the bottle through a directing nozzle up into the nose and its nasal-nasopharyngeal cavities and, in some treatments, towards the back of the throat for coating of the tongue area proximate the nasal-nasopharyngeal cavities.

The manually squeezed spray bottle device and method, however, have several drawbacks and are not suitable for all potential users. Many of these drawbacks are due to the fact that the user applies an unregulated force to squeeze the spray bottle, thus making the amount of fluid or dosage of spray administered to the nose not precisely determinable. The uncontrolled amount of force being applied may also causes problems in damaging sensitive nasal membranes due to too much force being applied, or even a back flow of fluid and possibly nasal mucous onto the user. The insertion of a nozzle or tube into the nose or its nasal-nasopharyngeal cavities may also cause irritation or injury to an area already compromised by illness.

DESCRIPTION OF THE PRIOR ART

Colds and influenzas are infectious viral diseases spread through contact, such as by touching virus contaminated surfaces, or by inhalation of airborne virus contaminated particles spread by coughing or sneezing. Each year approximately 65 million individuals catch colds and some 108 million catch influenza making it more than a mere annoyance but a yearly plague. Untreated influenza may even lead to death as was the case for many without money to pay for medicines or doctors in the early part of the $20^{th}$ century.

The cure for the common cold continues to evade the best efforts of medical science because the rhinovirus, believed to cause the diseases commonly referred to under the collective label of "a cold," is well adapted to a human host. The virus attaches itself to the adhesion molecules that hold immune-system cells to the lining of the respiratory tract. When the immune system begins to attack the invading virus, it creates more immune system cells that have to be held in place on the lining of the respiratory tract by more adhesion molecules, thus giving the virus more places to grow. Eventually the immune system defeats the virus by sloughing off the invading virus cell into the nasal discharge normally associated with colds. Conventional treatments are directed at assisting the removal of the virus cells by the immune system process by either attacking the virus cells directly or by assisting the immune system in sloughing off the infected respiratory tract lining.

The conventional state of the art attempts to implement this treatment procedure with a number of standard procedures. One common treatment procedure requires the patient to rest and drink large amounts of liquids along with dosages of aspirin, ibuprofen or acetaminophen to relieve what are common cold symptoms of fever and body aches. The rest and hydration allows the body to focus energy to the immune system reaction. The hydration additionally allows nasal discharges without a concurrent dehydration occurring.

Another treatment procedure used to fight colds and influenza attacks includes giving the patient an influenza vaccine in the form commonly known as a "flu shot." However, while "flu shots" are effective in preventing the diseases in 70 to 90 percent of healthy adults, since colds and influenzas are caused by a viral infection, antibiotics are of little or no value unless the cold or influenza also gives rise to a bacteria infection such as sinus and inner ear infection.

Many suffers resign themselves to their fate and wait for the cold or influenza to pass of its own accord. These individuals self-diagnose themselves and turn to over-the-counter decongestants and cough suppressants which may ease symptoms, but have various side effects such as drowsiness, nausea, etc. Some of these self-prescribed cures are actually counterproductive to fighting the illness. For example, decongestants such as antihistamines reduce the "runny nose" and "watery eyes" symptoms providing some apparent relief to the cold suffer. However, reducing the "runny nose" actually slows down the removal of the attacking virus, as watering of the eyes and nasal discharge are the body's main natural defense to remove the virus.

The foregoing discussion shows that a need exists for an alternative or additional treatment that does not tamper with the body's natural immune system processes and instead assists the immune system by removing the attacking virus quickly before it has a chance to spread and multiply.

The novel system of the present invention assists the immune system by removing the attacking virus cells when they initially attach themselves to the adhesion molecules in the respiratory tract areas in the nasal-nasopharyngeal cavities or throat, before the invading cells have a chance to multiply and cause the immune system response to generate more adhesive molecules suitable for additional viral growth.

SUMMARY OF THE INVENTION

It is, therefore, one of the principal objects of the present invention to provide a nasal-nasopharyngeal irrigating and cleansing system that assists the immune system by removing the attacking virus cells when they initially attach themselves to the adhesion molecules in the respiratory tract areas in the nasal-nasopharyngeal cavities or throat, before the invading cells have a chance to multiply and cause the immune system response to generate more adhesive molecules suitable for additional viral growth.

Another object of the present invention is to provide a method of using the nasal-nasopharyngeal irrigating and cleansing system of the present invention to assist the immune system by removing the attacking virus cells when they initially attach themselves to the adhesion molecules in the respiratory tract areas in the nasal-nasopharyngeal cavities or throat, before the invading cells have a chance to multiply and cause the immune system response to generate more adhesive molecules suitable for additional viral growth.

These and other objects are attained by the present invention which, in the broadest sense, comprises a cup having a bottom wall and front, first and second sidewalls. There is a sealing rim on the front wall which extends at least partially along the sidewalls for maintaining a watertight seal between the sealing rim and a user's face when the cup is rotated from a generally upright position to a generally horizontal position to allow pouring of a liquid held in the cup into the user's nasal and sinus cavities. Another aspect of the present invention is found in a method for nasal-nasophryngeal irrigating and cleaning of a user's nasal and sinus cavities with a solution, that comprises the steps of: placing the solution in a cup having a sealing rim for maintaining a watertight seal against a user's face when the cup is rotated from a generally upright position to a generally horizontal position; inserting the user's nose into the solution in the cup while holding the cup in a generally vertical orientation; rotating the cup from a generally vertical orientation to a generally horizontal orientation while maintaining a watertight seal between the sealing rim of the cup and the user's face; and, inhaling the solution from the cup into the user's nasal and sinus cavities.

Various additional objects and advantages of the present invention will become apparent from the following detailed description.

DETAILED DESCRIPTION OF THE PREFERRED EMBODIMENT

Figure 1:
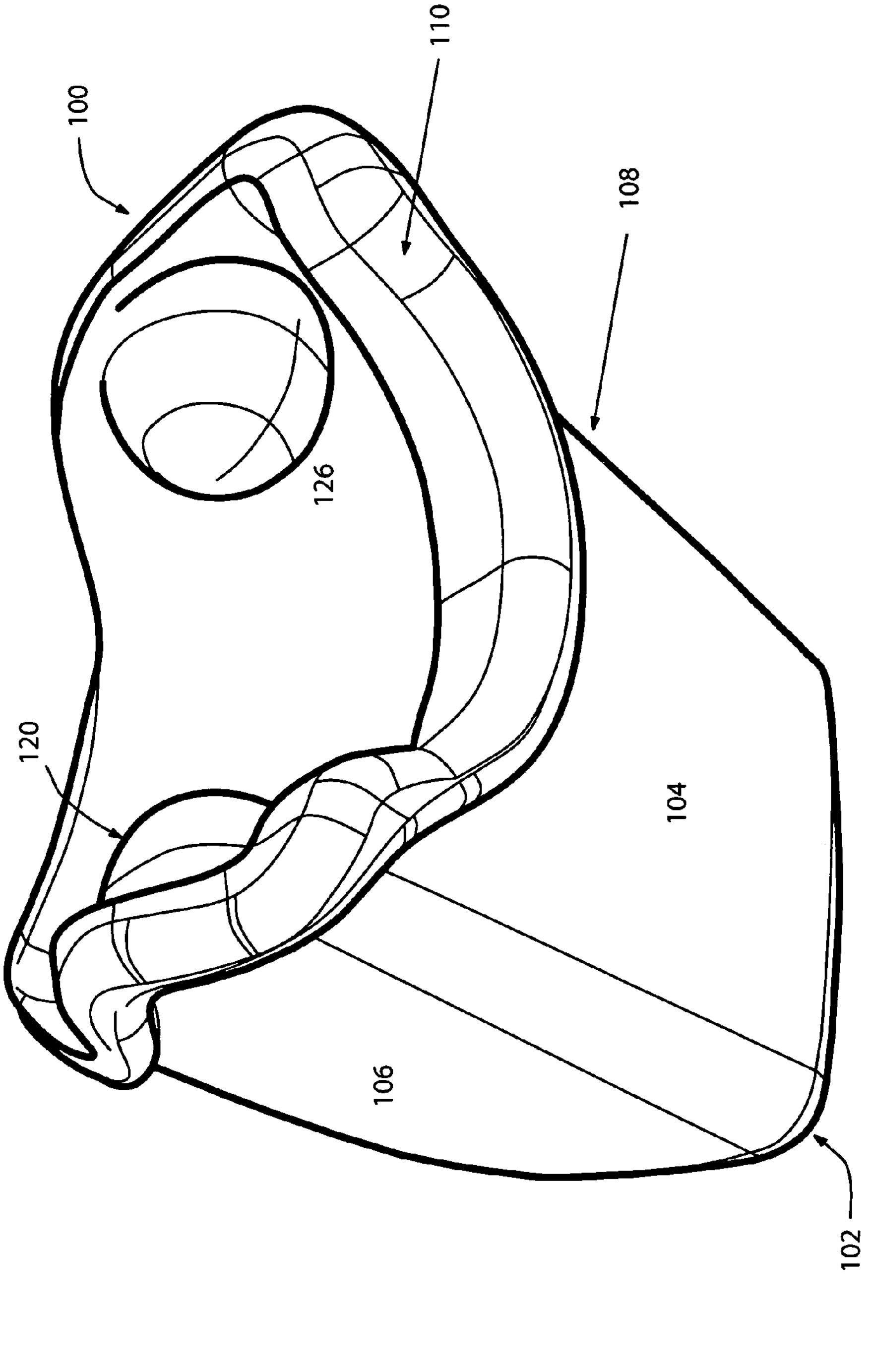
FIG. 1 is a perspective view of a device embodying the present invention.
Figure 2:
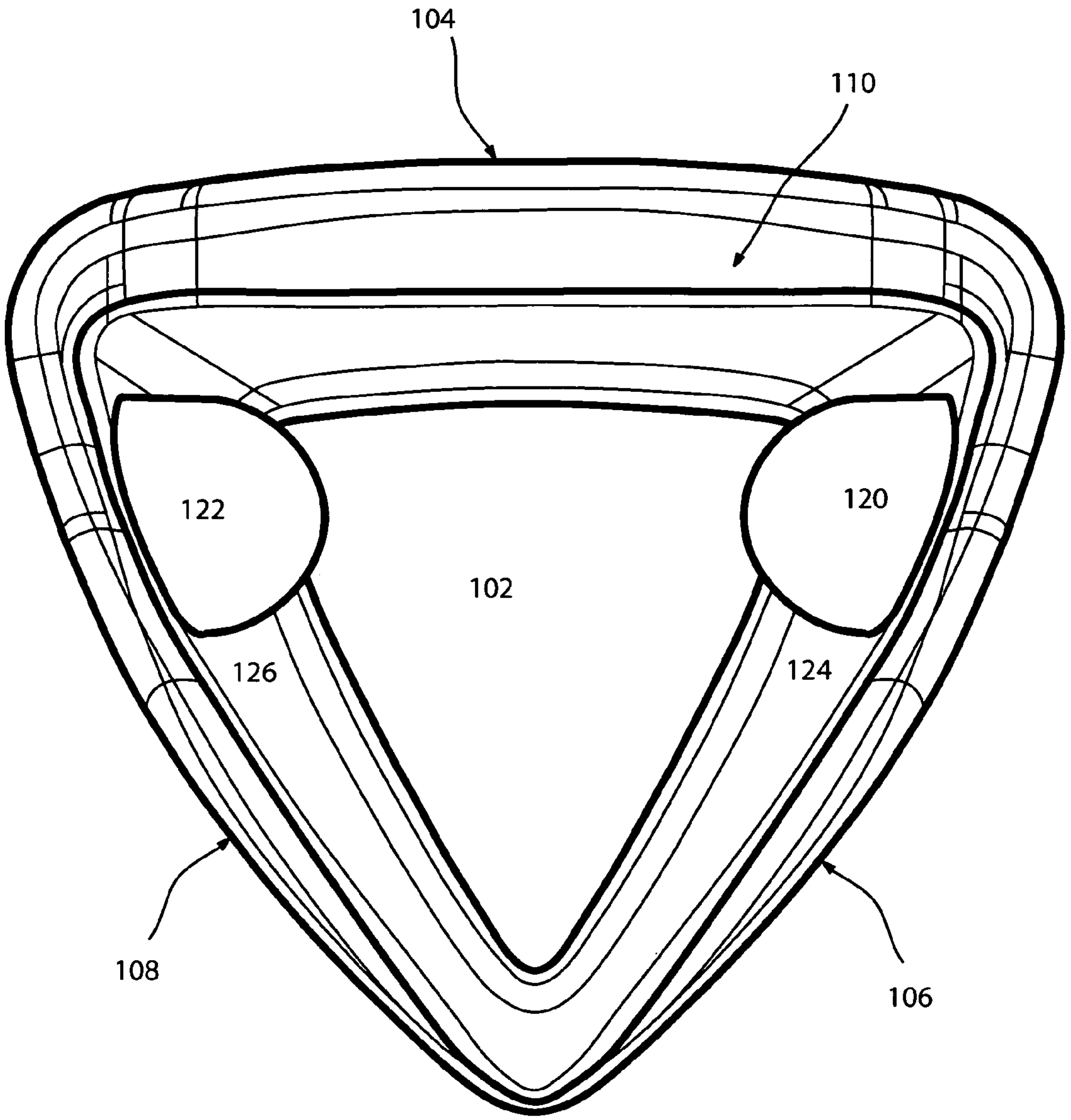
FIG. 2 is a top plan view looking into the device of FIG. 1.

Referring now to the Figures, a device embodying the present invention is shown generally at 100. The device is a cup having a bottom wall 102 and front, first and second sidewalls 104, 106 and 108, respectively. While the preferred cup has a generally triangular in cross-section for ease in grasping by a user's hand, similar easy to grasp cups having a shape adapted for grasping by a user, including, but not limited to oval or polygonal cross-sectional shapes, are also within the scope of the present invention.

The front 104 and sidewalls 106 and 108 have no openings therein. Additionally, the width of first and second sidewalls 106, 108 respectively, best seen in FIG. 4, preferably vary from a maximum width (at 112) where the sidewalls join the front wall 104 to a minimum width (at 114) where sidewalls 106 and 108 join one another. The preferred embodiment of a device 100 embodying the present invention has width of sidewalls 106 and 108 vary in order to create a vertical sidewall 116 as the cup is rotated from a generally upright position to a generally horizontal position. Vertical sidewall 116 allows the cup to continue to contain the liquid in the cup when the cup is rotated by the user to place his nose into the liquid, as first and second sidewalls 106, 108 are now in a horizontal position and no longer create a cavity for holding the liquid contained in the cup.

The cup has a sealing rim 110 on front wall 104 which extends, at least partially, along first and second sidewalls, 106 and 108 respectively, in order to maintain a watertight seal between sealing rim 110 and a user's face when the cup is rotated from a generally upright position to a generally horizontal position to allow pouring of a liquid held in the cup into the user's nasal and sinus cavities.

Figure 3:
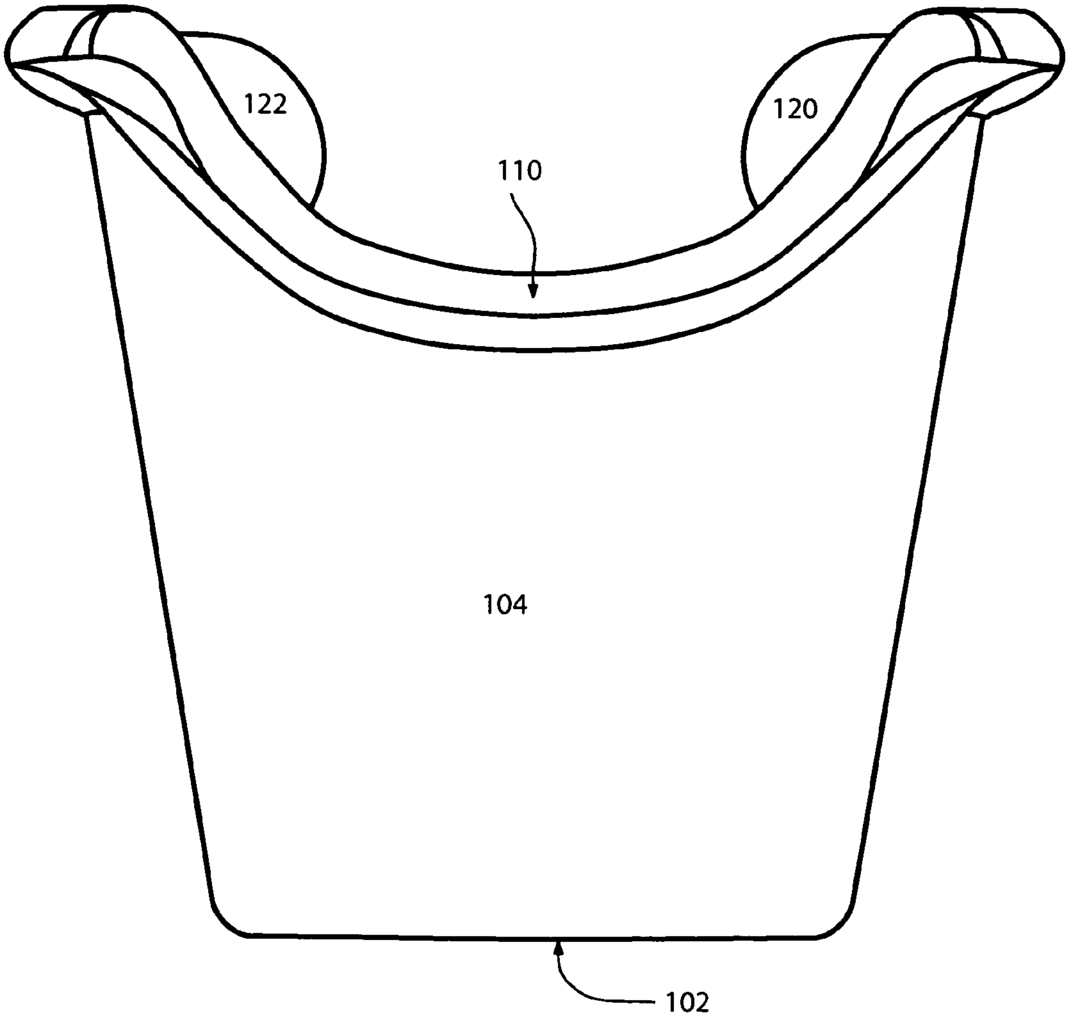
FIG. 3 is a front view of the device of FIG. 1.
Figure 4:
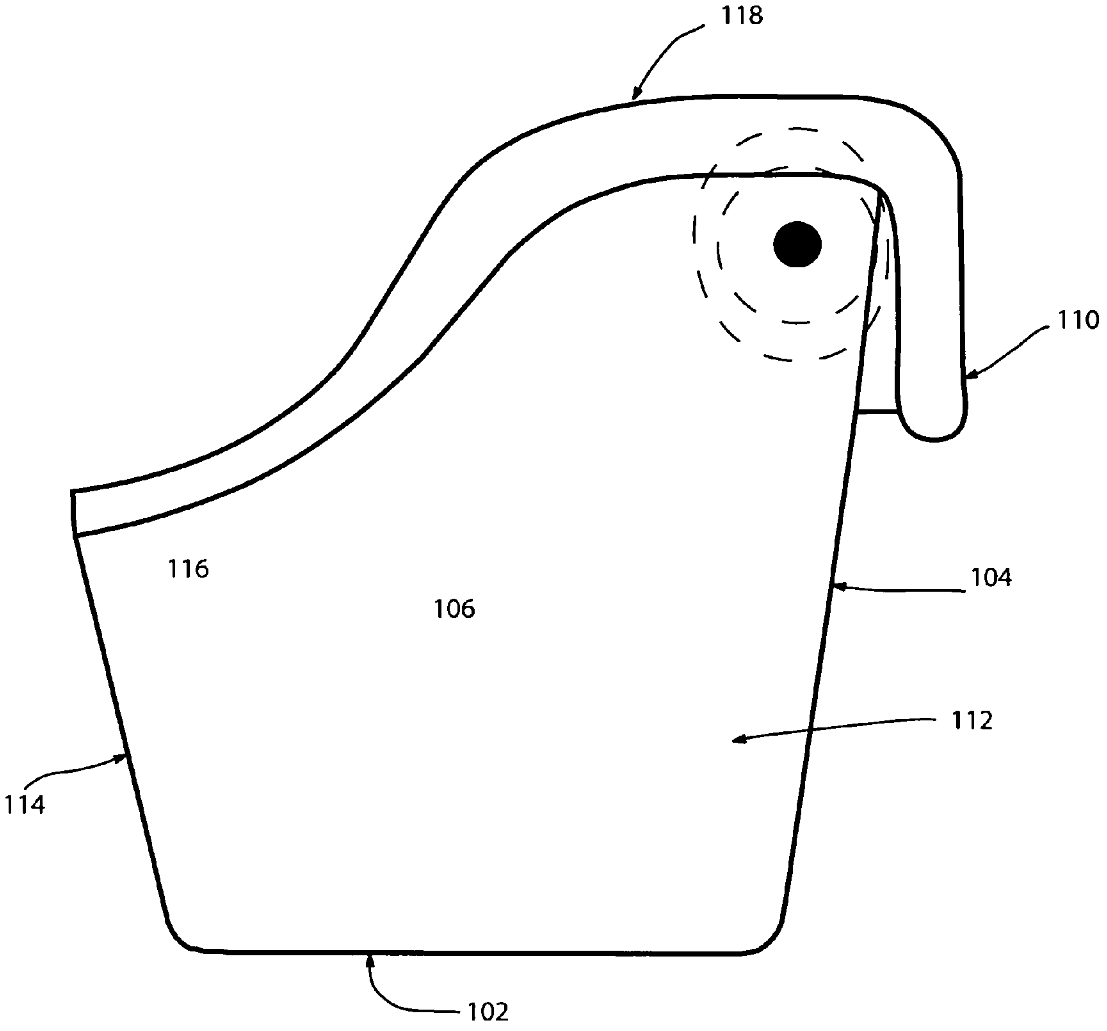
FIG. 4 is a side view of the device of FIG. 1.

One preferred shape for sealing rim 110 is to extend the rim so that it curves outwardly and downwardly away from the cup as best illustrated in FIGS. 1, 3 and 4. This configuration allows the cup rim to maintain a seal between sealing rim 110 and a user's face when the cup is rotated from a generally upright position to a generally horizontal position to allow pouring of a liquid held in the cup into the user's nasal and sinus cavities.

Sealing rim 110 preferably further includes a less curved, or somewhat flattened area 118 that is adapted to mate with a user's facial structure and act as a stop or brake to prevent further rotation of the cup on the user's face beyond a selected angle so as to maintain a sealing surface between sealing rim 110 and a user's face when the cup is rotated from a generally upright position to a generally horizontal position to allow pouring or inhaling of a liquid held in the cup into the user's nasal and sinus cavities.

Additionally to assist the user in selecting and controlling the flow of liquid into a particular nasal passage, it is preferred that the cup have a first and second protuberance 120 and 122, respectively, on the interior sides 124, 126 of first and second sidewalls 106, 108, respectively. Protuberances 120, 122 are positioned to allow a user to select either one of these protuberances to press against and close off a user's nostril allowing liquid held in the cup to flow through only the unclosed nostril into the nasal cavities at a time. The user can also choose not to utilize either of these protuberances and allow liquid to flow into both nasal passages simultaneously if so desired.

Additionally, alternate preferred embodiments of the present invention include further adding a vibrating device, such as an electric motor assembly that is attached to the bottom wall of the cup for vibrating a fluid held in the cup interior. The vibrator may be either integrally formed with the cup wall or may be a releasable unit that is attached to the cup when desired and removed when no longer needed.

One preferred embodiment of such a desirable vibrator device is an offset cam placed on the rotor of a small electric motor. The battery compartment can be formed in the base or bottom wall of the cup. The offset cam and motor assembly can be placed inside a rubber compartment placed in the bottom of the cup and pass its vibrations through a membrane into the liquid contained in the cup. Thus the liquid not the cup is vibrated. This arrangement requires a battery compartment and electric motor that are isolated inside a separate compartment from the liquid in the cup by an O-ring seal. The offset cam causes the whole assembly, including the battery to vibrate. Alternative embodiments include mounting the motor and battery to the cup body with an offset cam moving a diaphragm to cause the liquid to vibrate. The vibration is set to cause the liquid held in the cup and nasal passages to oscillate back and forth across the celphila hairs found in the nasal passages, thereby loosening and pulling the virus infected mucous into the liquid for removal. Vibratory removal and loosening of the infected materials in the nasal passages works best when there is a continuous liquid path from the liquid held in the cup into the nasal passages so that the induced vibrations can be passed effectively.

A self-contained vibrating unit is also encompassed within the scope of the present invention. Such a self-contained vibrating unit contains an offset motor that is sealed inside a container with a battery for its power source. An On/Off switch is mounted on the outside of the container and an aperture is closed with O-ring seal on the container to allow access for replacement of the battery. The battery size should be selected to overcome the limited air space buoyancy of the unit. The benefit of the vibration element floating in the solution is the efficiency increase over one that is attached to the cup body. If the vibrating assembly is mounted on the cup body, a large amount of the vibrating energy would be lost vibrating the cup body and the hand holding it. A self-contained vibrating module not attached to the cup body will push energy into the liquid with little loss vibrating the cup or hand holding the cup. The motor speed and offset are designed for an optimally resonant frequency of the liquid in the cup and in the nasal passage. A continuous liquid path or connection must be maintained from the vibrating module into the liquid in the nasal passage for best results. The vibration washes the liquid abrasively back and forth across the nasal hairs that have trapped the virus or other undesirable particles in the nasal passages.

Figure 5:
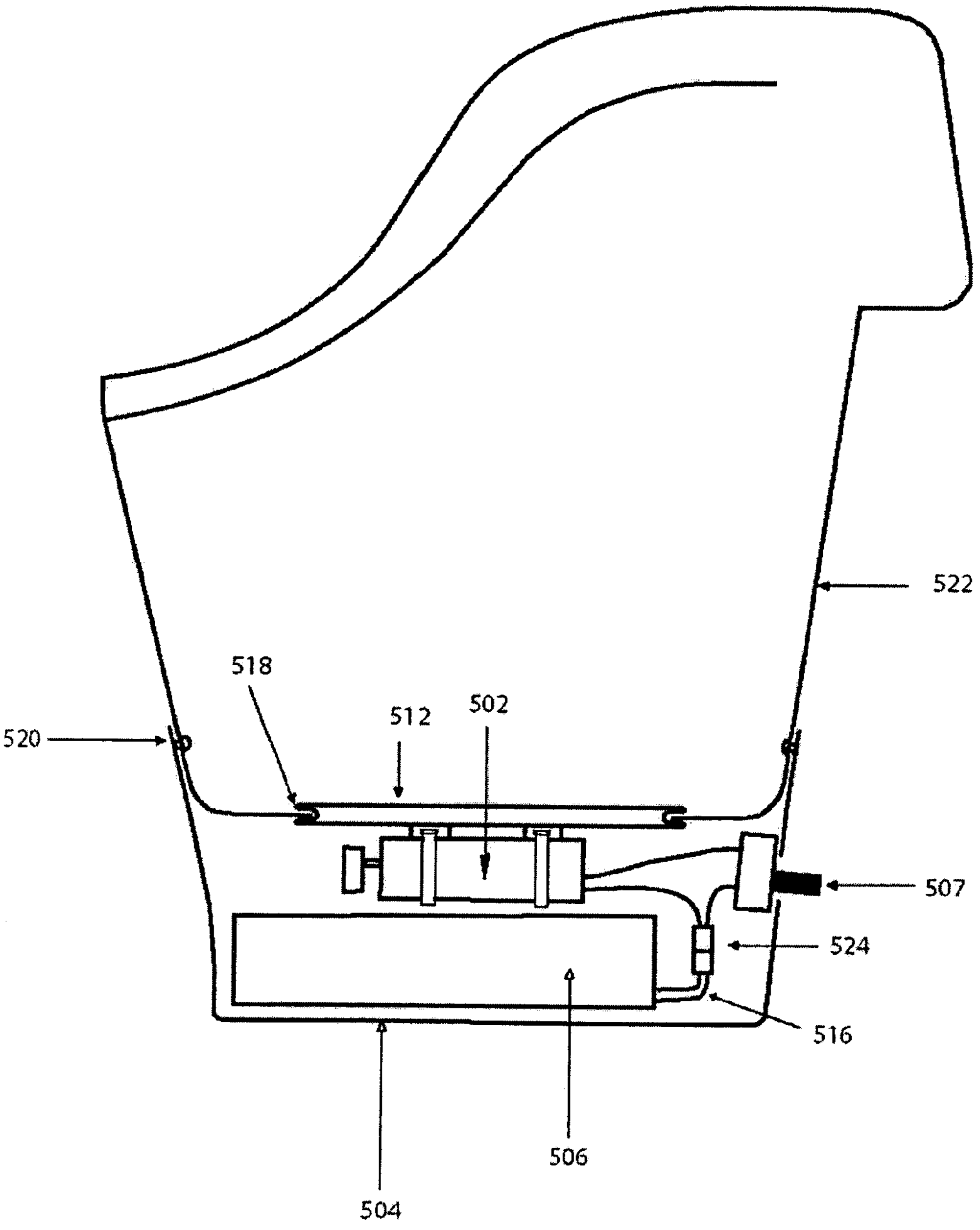
FIG. 5 is an idealized side cross-sectional view of a device embodying the present invention showing a vibrating means; and, FIG. 6 is an idealized side cross-sectional view of a device embodying the present invention showing a heating means.

One preferred embodiment of such a self-contained vibrating unit is illustrated in FIG. 5 and designated generally by reference numeral 500. Such a self-contained vibrating unit 500 utilizes a clip-in mechanism 520 to mount it to cup 522. Unit 500 contains an offset motor 502 that is sealed inside a container 504 with a battery 506 for its power source. A release connector 524 may be interposed in wiring 516 to facilitate changing of battery 506. Offset motor 502 is mechanically connected to diaphragm 512 by tie wraps and electrically to battery 506 by wiring 516. Diaphragm 512 may be elastically attached to the cup by an adhesive, such as Bostic 2402 glue or any other similar elastic adhesive around the periphery 518 of diaphragm 512.

Likewise, another alternate preferred embodiment includes heating the liquid held in the cup by attaching to the cup sidewalls a heater device, such as an electric heating element adapted for insertion into the interior of the cup and submersion into the liquid held in the cup.

Figure 6:
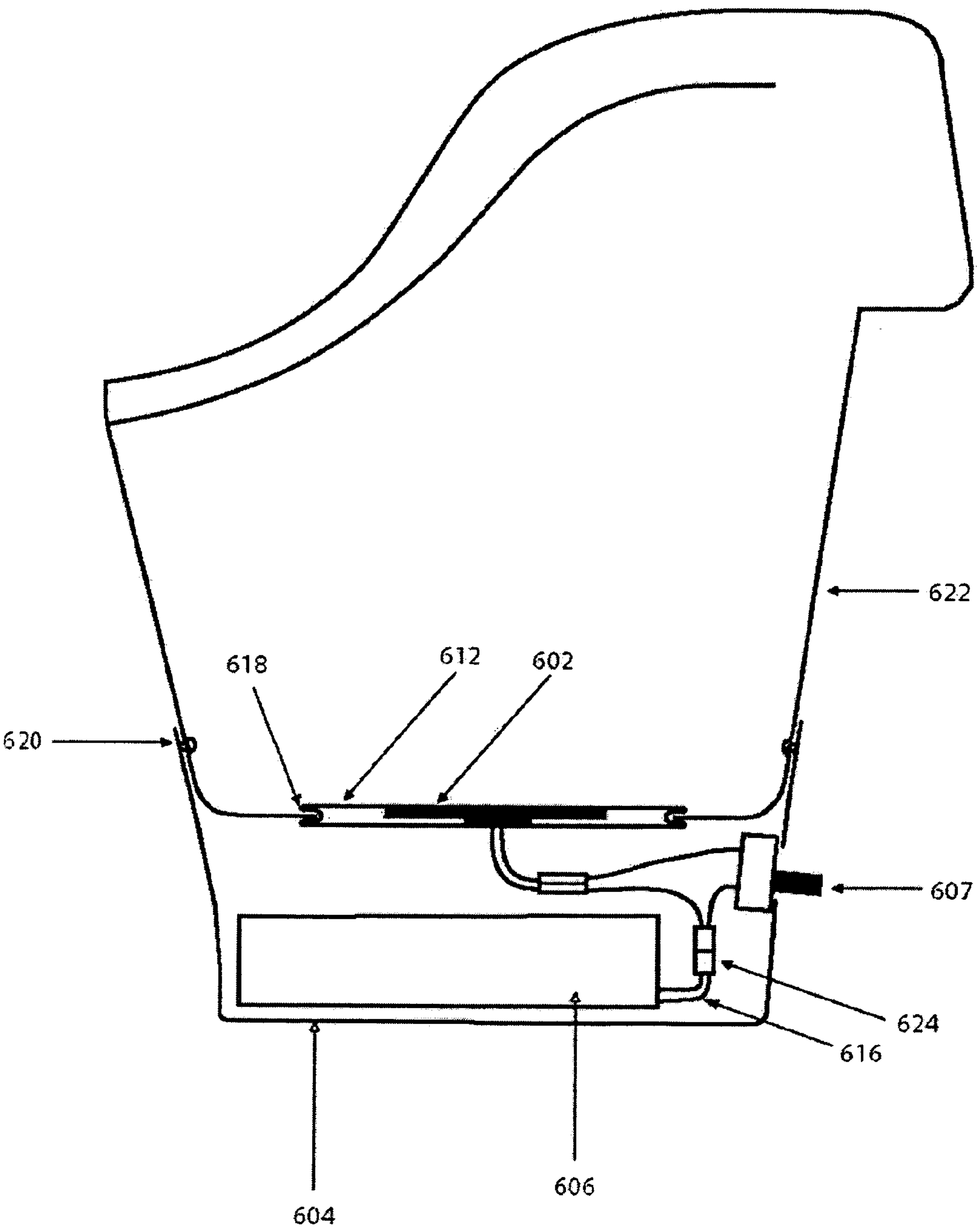

One preferred embodiment of such a heating unit is illustrated in FIG. 6 and designated generally by reference numeral 600. Such a heating unit 600 utilizes a clip-in mechanism 620 to mount it to cup 622. Unit 600 contains a heating element 602 that is sealed inside a container 604 with a battery 606 for its power source. A release connector 624 may be interposed in wiring 616 to facilitate changing of battery 606. Heating element 602 is embedded in wall portion 612. Wall portion 612 may be elastically attached to cup 622 by an adhesive, such as Bostic 2402 glue or any other similar elastic adhesive around the periphery 618 of wall portion 612.

Additionally, a splash barrier that partially covers the cup mouth, is also within the scope of this invention, as it would protect a user's facial area adjacent the cup mouth during use from spillage of liquid held contained in the cup when said cup is rotated too rapidly.

The present invention is also embodied in a method for nasal-nasophrryngeal irrigating and cleaning of a user's nasal and sinus cavities with a cleansing, irrigating, or medicinal solution. One preferred embodiment of such a method comprises the steps of:

placing the selected liquid solution in a cup having a sealing rim for maintaining a watertight seal against a user's face when the cup is rotated from a generally upright position to a generally horizontal position;

inserting the user's nose into the solution in the cup while holding the cup in a generally vertical orientation;

rotating the cup from a generally vertical orientation to a generally horizontal orientation while maintaining a watertight seal between the sealing rim of the cup and the user's face;

inhaling the solution from the cup into the user's nasal and sinus cavities.

holding the solution in the user's nasal and sinus cavities for a desired period of time; and, expelling the solution held in the user's nasal and sinus cavities by the user exhaling through his nose.

Alternatively, in place of the step of expelling the solution by exhaling through the user's nose, the method includes the step of draining the solution held in the user's nasal and sinus cavities by tilting the user's head to allow gravity to cause the solution to drain out.

An example of how the device of the invention and process described above are used in practice is now given.

A user will first partially fill the cup of the invention with the desired liquid irrigating, cleansing or medicinal solution. As a start, the user may wish to select a liquefying solution designed to soften dried mucous and nasal tissue membranes. The user now places the cup of the invention against his upper lip using the sealing surface described. The user then rotates his nose into the cup until his nasal passages are submerged into the liquid solution inside the cup interior. The cup can then be titled towards the user's face while maintaining the sealing surface so that the liquid does not leak out and spill against the user's face. The user can hold this tilted position allowing the solution to reach and soften the dry mucus. When able, the user can inhale the solution by sniffing the liquid further into the nasal passages.

The user can hold the solution in his nasal passages by inhaling slightly, thereby creating a vacuum. After a few minutes, the solution loosens the mucus and can be exhaled from the nasal passages.

To ensure both nasal passages are clearing, the user can move the nose to one side of the cup pressing against the nasal stops or protuberances as discussed above. Pressing one nostril against the nasal blocking protuberance blocks the nasal passage forcing the solution into the other unblocked nasal passage. This process of inhaling and exhaling the solution is continued until the solution has cleared to the top of the nasal cavity and is starting to reach the back of the throat.

Now the nasal passages are moist, the user preferably replaces the liquefying solution with a flushing solution and repeats the process. The flushing solution is selected to be more abrasive than the liquefying solution. It is used to remove any virus cells attached to the back of the throat which communicates with the nasal passages. This requires that the flushing solution be drawn up the nasal passage by sniffing and down the throat into the mouth. The user employs the nasal stop protuberances to ensure both nasal passages are flushed. The complete solution should be used repeated as necessary.

Now that the nasal passages have been moistened and flushed, the user preferably replaces the flushing solution with an antiviral solution. This solution is designed to attack any of the remaining virus cells that have not been removed by the flushing process. These may be strongly attached at the back of the throat and in the process of reproducing. The antiviral solution damages the viral cell membrane stopping reproduction and killing the virus. The anti-viral solution is preferably repeatedly flushed through the nasal and throat passages by sniffing it into the nasal passages to the throat passage to coat all surfaces that may be contaminated with the virus. The user would preferably rotate the position of his head to ensure complete coating of the nasal passageways.

Finally, when the nasal and throat passages are filled with the anti viral solution, the user can stop the inhaling process but preferably does not exhale the solution. Some of the solution will drop from the nasal passages when the user stops inhaling, but the upper nasal passages will hold the solution. The solution can be maintained in the nasal passages overnight or until it is desired to expel it by exhaling as detailed above. Holding the antiviral solution in the nasal passages prevents any additional viral infection as the invading viri are blocked by the antiviral solution retained in the nasal passages.

In view of the above, it will be seen that the several objects of the invention are achieved and other advantageous results attained.

As various changes could be made in the above construction and methods without departing from the scope of the invention, it is intended that all matter contained in the above description or shown in the accompanying drawings shall be interpreted as illustrative and not in a limiting sense.

What is claimed is:

1. A nasal-nasopharyngeal irrigating and cleansing system comprising:

a cup, generally triangular in cross-section for ease in grasping by a user's hand, having:

a bottom wall;

a front, first and second sidewalls, said sidewalls having no openings therein and the width of said first and second sidewalls varying from a maximum width where said sidewalls join said front wall to a minimum width where said sidewalls join one another, the varying width of said sidewalls creating a horizontal sidewall as the cup is rotated from a generally upright position to a generally horizontal position for maintaining a cavity to contain the liquid held in the cup as the original first and second sidewalls no longer create a cavity for holding the liquid;

a sealing rim on said front wall and extending at least partially along said first and second sidewalls, said sealing rim including an area adapted to mate with a user's facial structure to prevent further rotation of said cup on the user's face beyond a selected angle so as to maintain a sealing surface between said sealing rim and a user's face when said cup is rotated from a generally upright position to a generally horizontal position while the user's head is held at least generally upright or rearwards to allow pouring by gravity flow during rotation of the cup with regard to the user's face of a liquid held in the cup into the user's nasal and sinus cavities;

a first and second protuberance on the interior side of said first and second sidewalls respectively, adapted to allow a user to select one of said protuberances to press against and close off a user's nostril allowing liquid held in the cup to flow through only the unclosed nostril into the nasal cavities.

2. A nasal-nasopharyngeal irrigating and cleansing system as in claim 1 further comprising means attached to said cup for vibrating a fluid held in the interior of said cup.

3. A nasal-nasopharyngeal irrigating and cleansing system as in claim 2 wherein said vibrating means is integrally formed on said bottom wall of the cup.

4. A nasal-nasopharyngeal irrigating and cleansing system as in claim 2 wherein said vibrating means is releasably attached to said bottom wall of the cup.

5. A nasal-nasopharyngeal irrigating and cleansing system as in claim 2 wherein said vibrating means is releasably attached to said bottom wall of the cup comprises an electric vibrating motor assembly.

6. A nasal-nasopharyngeal irrigating and cleansing system as in claim 1 further comprising means for vibrating a fluid held in the interior of said cup.

7. A nasal-nasopharyngeal irrigating and cleansing system as in claim 6 wherein said vibrating means is a self-contained electric vibrating motor assembly designed for insertion into the interior of said cup and at least partial submersion into the liquid contained therein.

8. A nasal-nasopharyngeal irrigating and cleansing system as in claim 1 further comprising means for heating a liquid held in said cup.

9. A nasal-nasopharyngeal irrigating and cleansing system as in claim 5 wherein said heating means further comprises:

an electric heating element adapted for insertion into the interior of said cup and submersion in the liquid held in said cup.

10. A nasal-nasopharyngeal irrigating and cleansing system as in claim 5 further comprising:

a splash barrier, partially covering the mouth of said cup, for protecting a user's facial area from spillage of liquid held contained in said cup when said cup is rotated too rapidly.

* * * * *